United States Patent [19]
Ishihara et al.

[11] Patent Number: 5,241,473
[45] Date of Patent: Aug. 31, 1993

[54] ULTRASONIC DIAGNOSTIC APPARATUS FOR DISPLAYING MOTION OF MOVING PORTION BY SUPERPOSING A PLURALITY OF DIFFERENTIAL IMAGES

[75] Inventors: Ken Ishihara, 1-15, Chiguso-1-Chome, Takarazuka-shi; Hiroya Kondo, Osaka; Akihiro Ueyama, Tama; Toshio Ogawa, Inba; Shinji Kishimoto, Tsukuba, all of Japan

[73] Assignees: Ken Ishihara; Hitachi Medical Corporation, Tokyo, Japan

[21] Appl. No.: 775,000

[22] Filed: Oct. 11, 1991

[30] Foreign Application Priority Data

Oct. 12, 1990 [JP] Japan .................................. 2-272315
Nov. 8, 1990 [JP] Japan .................................. 2-301103

[51] Int. Cl.$^5$ ........................ G06F 15/00; A61B 8/00; H04N 5/31
[52] U.S. Cl. ............. 364/413.25; 128/660.01; 358/112
[58] Field of Search .............. 364/413.25, 414, 413.13; 128/660.01, 642, 660.05, 661.02, 661.09, 654; 73/626, 628, 602; 358/112, 167; 606/130

[56] References Cited
U.S. PATENT DOCUMENTS

| | | | |
|---|---|---|---|
| 4,205,687 | 7/1980 | White et al. | 128/661.09 |
| 4,463,425 | 7/1984 | Hirano et al. | 364/413.05 |
| 5,060,515 | 10/1991 | Kanda et al. | 128/661.01 |

Primary Examiner—Roy N. Envall, Jr.
Assistant Examiner—Khai Tran
Attorney, Agent, or Firm—Antonelli, Terry, Stout & Kraus

[57] ABSTRACT

The present invention includes an ultrasonic diagnostic apparatus for forming differential image data by performing differential operation among topographic image data obtained in time series, an apparatus for giving color codes which designate display colors to differential image data, an apparatus for cumulating a plurality of frames of differential image data, and an apparatus for displaying respective cumulated differential images in colors designated by the color codes in which motion of a moving portion of a patient's body is displayed in colors by superposing a plurality of differential images.

9 Claims, 15 Drawing Sheets

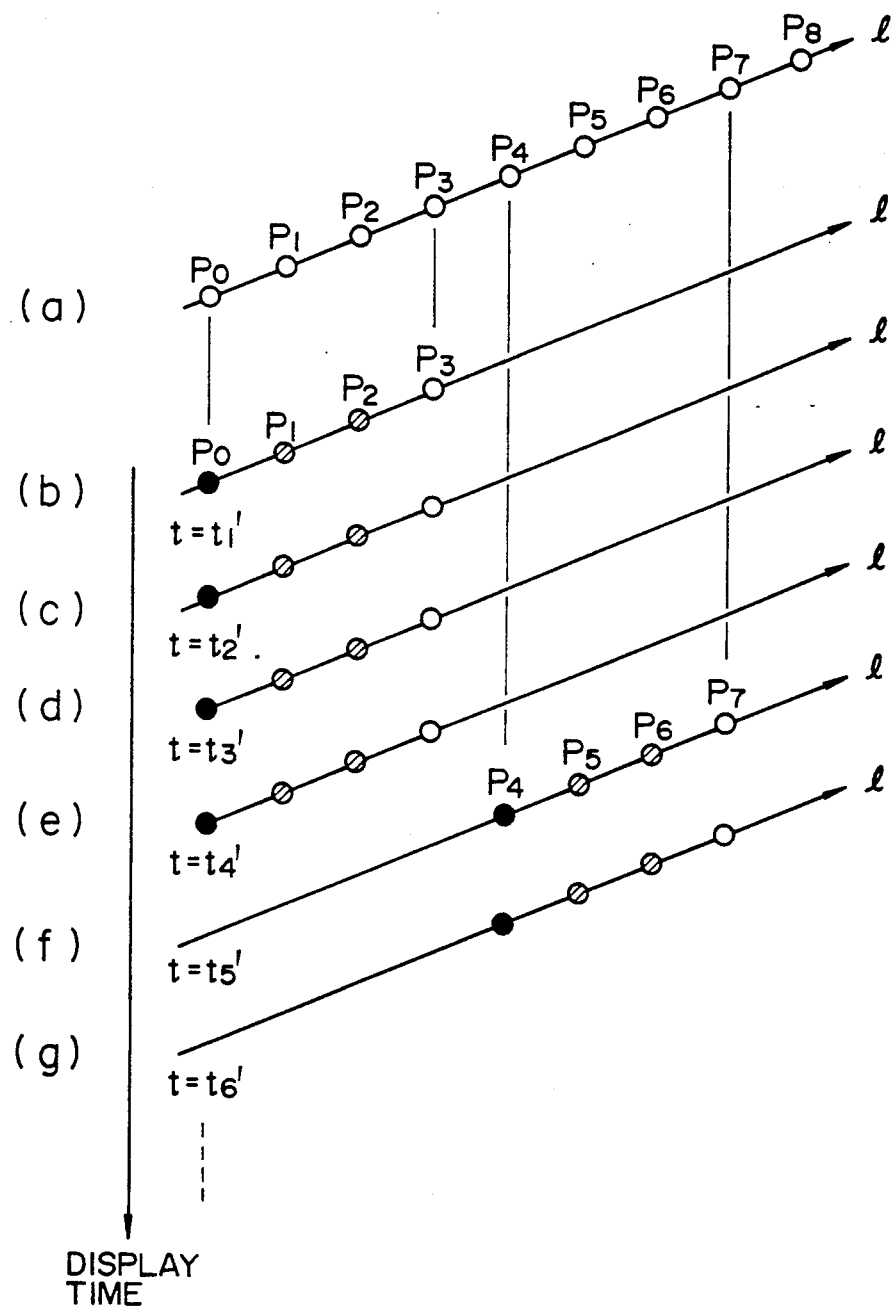
F I G. 16

ULTRASONIC DIAGNOSTIC APPARATUS FOR DISPLAYING MOTION OF MOVING PORTION BY SUPERPOSING A PLURALITY OF DIFFERENTIAL IMAGES

BACKGROUND OF THE INVENTION

The present invention relates to an ultrasonic diagnostic apparatus for obtaining a topographic image with respect to a diagnostic portion of the body to be inspected by utilizing an ultrasonic wave, and more particularly to an ultrasonic diagnostic apparatus in which the motion of a moving portion such as a heart, a blood vessel and a blood stream in a body to be inspected can be depicted with colored differential images without using a contrast medium and a series of images of the moving portion can also be displayed on a scope.

B mode display, Doppler mode display and the like have been known as a method of displaying images of the blood stream, the heart and the like in the body to be inspected in real time by using an ultrasonic wave. An attempt to obtain differential images with ultrasonic topographic images is discussed in British Heart Journal 59 (1988) pp. 12-19. In this technique, a contrast medium is used and subtraction is made between topographic images before and after injection of the contrast medium so that observation may be made with contrast formed of a region of a heart for instance.

For example, in this method of image display, four frames of ultrasonic topographic images are taken before injecting the contrast medium into a body to be inspected and these four frames of images are added and averaged to form a mask image A as shown in FIG. 1. Then a contrast medium is injected into the body and topographic images ($B_1$, $B_2$, ... $B_n$) are taken after a lapse of time to allow the contrast medium to reach a portion of the body to be diagnosed, and subtraction is made between the mask image and respective topographic images after injection of the contrast medium so as to obtain differential images ($C_1$, $C_2$, ..., $C_n$) in consecutive order. Namely, the differential images are obtained in such a manner that $B_1 - A = C_1$, $B_2 - A = C_2$, ... $B_n - A = C_n$. In this method, the density of respective picture elements in the image which becomes the mask image is a mean value of the density of corresponding picture elements of the four frames. This method obtains better differential images by reducing effects of random noise affecting the differential images.

Further, an ultrasonic diagnostic apparatus which displays differential images is described in the 55th Proceeding of the Japan Society of Ultrasonics in Medicine (issued on Oct. 4, 1989) pp. 291-292, and in the 56th Proceeding of the Japan Society of Ultrasonics in Medicine (issued in May, 1980) pp. 351-354. Further, display of differential images in these ultrasonic diagnostic apparatus is made in such a manner that differentiation is obtained among tomographical images in a time series with the differential images being displayed one by one in consecutive order.

In the case of image display by such a conventional ultrasonic diagnostic apparatus, a contrast medium is injected into the blood of the patient so as to depict a location where blood is moving such as the ventricle and atrium by emphasizing the contrast. Therefore, it has been difficult to obtain movement information of a portion of the patient's body having small blood stream such as a tissue itself. Further, although the movement of an inner wall of a ventricle or atrium can be observed, the movement of the outer wall cannot be observed. Furthermore, since a contrast medium is injected into the patient, the conventional apparatus could not be used for patients who cannot tolerate injection of the contrast medium.

Further, it has been reported that real time differential image display is possible without using a contrast medium, and premature venticular contraction which has been impossible to observe with conventional topographic image display can be displayed on a scope. As a result, there is a possibility for developing a new field of ultrasonic diagnosis. However, since differential images are displayed one by one in consecutive order, the movement of a moving portion of the patient's body such as the internal organs is judged after the movement has occurred.

Namely, in the above-described conventional example, the movement in a time series of a moving portion of the body of a patient to be inspected is not displayed directly on a scope and is only judged relying on afterimage effects by observing the change in differential images displayed one by one in consecutive order. Thus, attention to the differential image is required, differences varying depending on the observer. Further, it is also desirable that a biosignal detecting section be provided so as to display an electrocardiogram of the patient as well as a display of the differential images. However timing of differential image relative to the electrocardiogram is unknown unless observation is made by contrasting the electrocardiogram with differential images one by one. Thus, diagnosis is difficult when the electrocardiogram must be considered in conjunction with the images.

An ultrasonic diagnostic apparatus which extracts differential images is described in JP-A-62-189054 or patent Application No. Hei 1-258352. In JP-A-62-189054, a method is disclosed in which a frame memory is provided and components of motion are extracted by displaying images applied with differential processing among respective frames. Further, in the Patent Application No. Hei 1-258352, a technique of applying differential processing among images which are adjacent in a time series, a technique of applying differential processing in optional time phase from images arranged in time series, and a technique of displaying differential images in colors are also disclosed.

In the above-described conventional techniques, differential processing is performed by using topographic image data, and the differential images are only displayed for each frame with no cumulative processing of a plurality of differential images being performed. Accordingly, it has been impossible to display velocity vectors (showing the size and the direction of velocity) of a moving portion of a patient's body and to perform kymographical observation of a blood stream for instance sufficiently.

SUMMARY OF THE INVENTION

Accordingly, it is an object of the present invention to provide an ultrasonic diagnostic apparatus in which the foregoing problems are solved in which movement of a moving portion of a patient's body such as a heart or blood vessels are depicted with colored differential images and display in a time series of the moving portion of the patient's body on a scope is produced, and it is further possible to discriminate timing of the images relative to a biosignal of the patient.

In order to achieve the above-described object, there is provided an ultrasonic diagnostic apparatus according to the present invention having ultrasonic transmitting-receiving circuit for transmitting and receiving an ultrasonic wave to the patient, a tomograph scanning circuit for obtaining topographic image data including data from moving tissues repeatedly at a predetermined period by using reflected echo signals from the ultrasonic transmitting-receiving circuit, a circuit for performing computation among images in a time series obtained by the tomograph scanning circuit to successively generate differential image data thereof, and an image display unit for displaying differential image data from the differential image data generating circuit. A circuit is provided for adding color codes giving different hues to the differential image data in the displayed images and circuit is provided for converting the differential image data added with the color codes into colors designated by the added color codes and also for superposing plurality of frames of differential image data with the superposed differential image data being displayed on the image display unit.

Further, offset is provided on the images which become the objects of differentiation and weighing is applied to the differential images and a plurality of sheets of differential images given with offset or applied with weighing are superposed. Thus, luminance levels are color-coded so that the magnitude and the direction of the velocity of a moving portion may be grasped easily on the display scope.

With this, it is possible to depict the motion of a moving portion of a body to be inspected with colored differential images, and also to display moving states in time series of the moving portion directly on a scope at the same time.

Accordingly, it is possible to observe directly the moving status of the moving portion and also to eliminate individual difference depending on observers without relying on the afterimage effects of humanvision.

Also, there are provided a sensor for detecting a biosignal with respect to the body to be inspected, a storage device which reads and writes the data of th detected biosignal synchronously with the topographic image data of the tomograph scanning circuit, and circuit for adding biosignal data from the storage device to the differential image data given with the color codes, and the differential image data corresponding one to one to respective portions of the biosignal data are read using the biosignal data of the storage device and color codes are added with the color code adding unit so as to change the color for each frame of the differential images in display.

With the invention it is possible to easily discriminate the timing of differential images relative to the biosignals from the patient. Accordingly, it is not required to contrast the electrocardiogram with the differential images on a one by one basis which reduces the attention required for diagnosis. As a result, diagnosis may be made easier according to an ultrasonic diagnostic apparatus of the present invention.

BRIEF DESCRIPTION OF THE DRAWINGS

FIG. 16 is a diagram showing another display example of cumulative differential images.

DESCRIPTION OF THE PREFERRED EMBODIMENTS

Embodiments of the present invention will be described in detail hereinafter with reference to the accompanying drawings.

Figure 1:
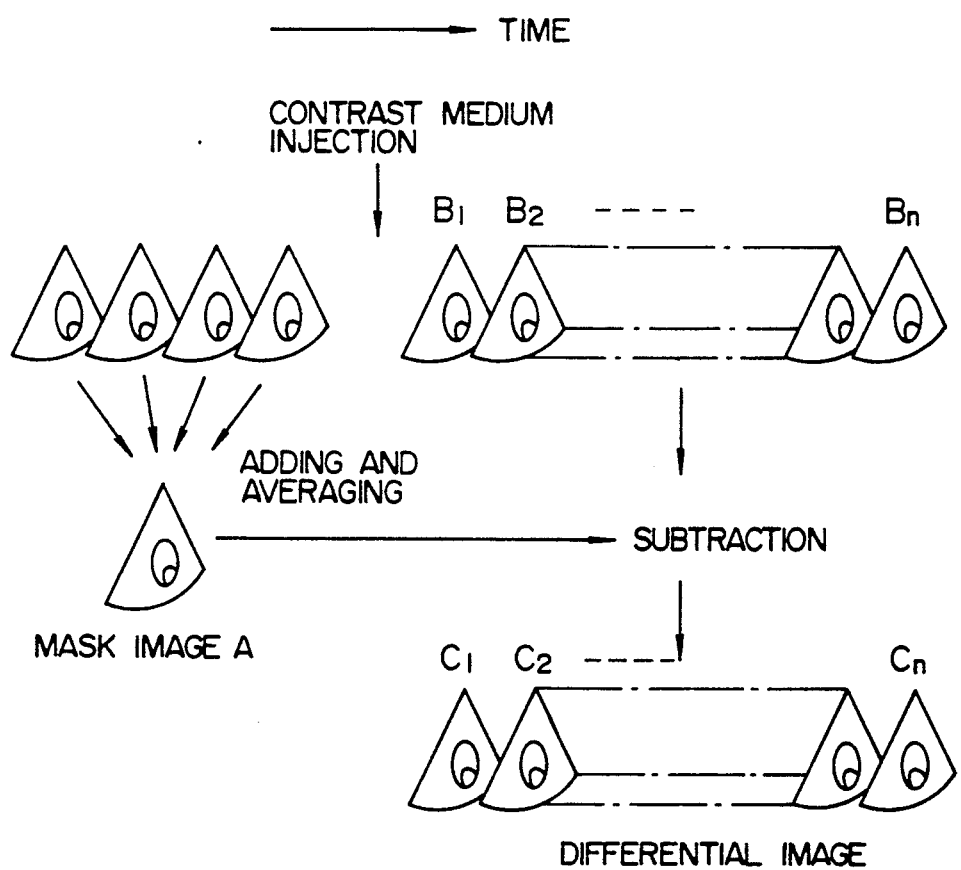
FIG. 1 is a diagram for explaining display operation of differential images in the prior art.
Figure 2:
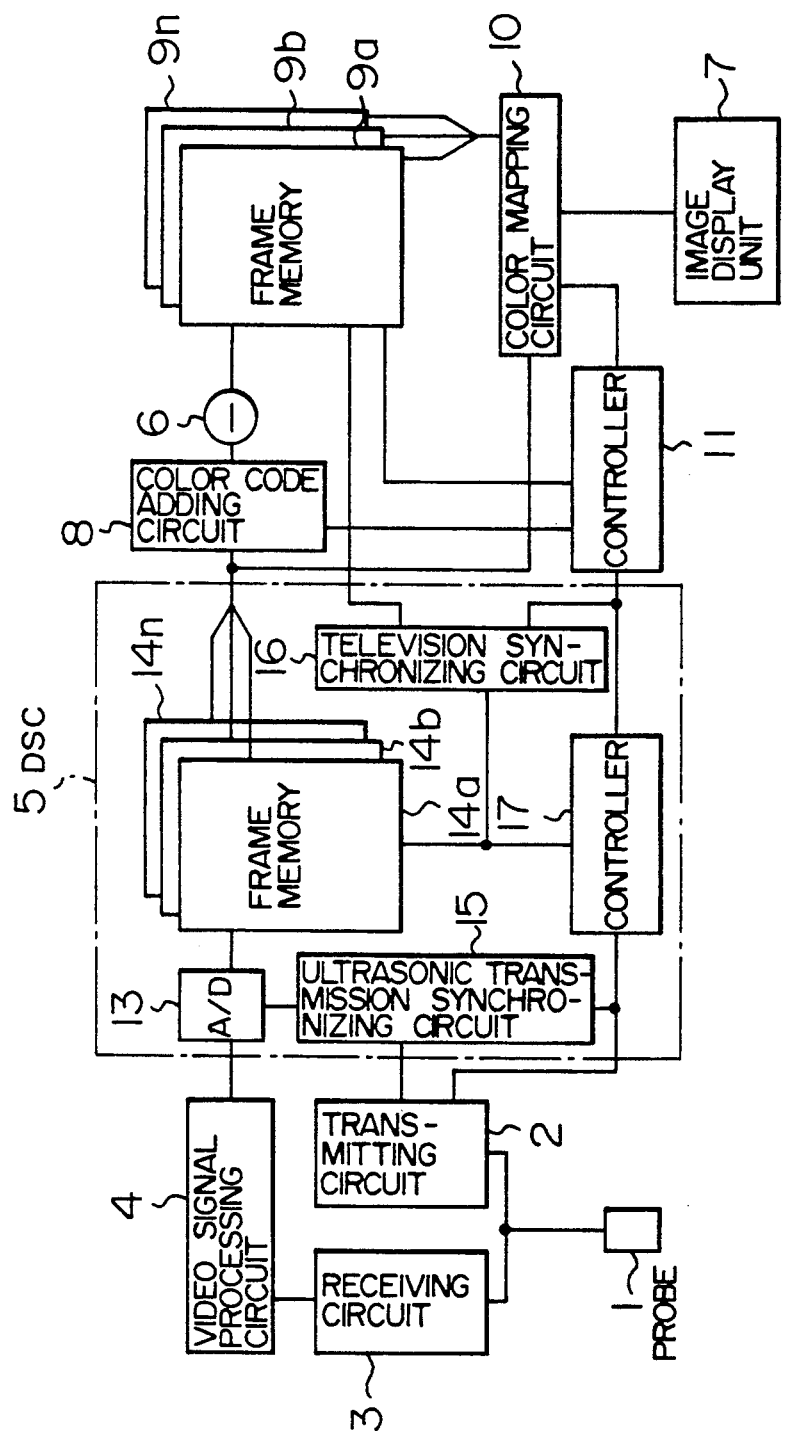
FIG. 2 is a block diagram of a first embodiment of an ultrasonic diagnostic apparatus according to the present invention.

FIG. 2 is a block diagram showing a first embodiment of an ultrasonic diagnostic apparatus according to the present invention. The ultrasonic diagnostic apparatus is for obtaining tomographical images with respect to a portion of a patient's body to be diagnosed by utilizing an ultrasonic wave. As shown in FIG. 2, it includes a probe 1, a transmitting circuit 2, a receiving circuit 3, a video signal processing circuit 4, a digital scan converter (hereinafter abbreviated as a "DSC") 5, a subtracter 6, and an image display unit 7, and is provided further with a color code adding circuit 8, frame memories 9a to 9n, a color mapping circuit 10 and a controller 11.

The probe 1 is for performing beam scanning mechanically or electronically so as to transmit and receive an ultrasonic wave to and from the patient's body and includes a vibrator (not shown) which generates an ultrasonic wave and receives a reflected echo. The transmitting circuit 2 drives the probe 1 so as to form a transmitting pulse for generating the ultrasonic wave and sets a convergent point of the ultrasonic wave transmitted from a transmitted wave phasing circuit contained inside to a certain depth in the patient's body. Further, the receiving circuit 3 amplifies a signal of a reflected echo received with the probe 1 at a predetermined gain and controls phases at one or a plurality of convergent points by means of a received wave phasing circuit to form an ultrasonic beam. Furthermore, the video signal processing circuit 4 receives a signal from the receiving circuit 3 and performs signal processing such as gain correction, log compression, edge enhancement and filter processing. Thus, the probe 1, transmitting circuit 2, receiving circuit 3 and video signal processing circuit 4 form ultrasonic transmitting-receiving circuit as a whole, and a frame of topographic image is obtained by having an ultrasonic beam scan in a certain direction in the body of the patient with the probe 1.

The DSC 5 obtains topographic image data of the body of the patient including data from moving tissue at an ultrasonic transmission period by using a reflected echo signal outputted from the video signal processing circuit 4 of the ultrasonic transmitting-receiving circuit and functions as a circuit for reading these data synchronously with a television display of these data and per-circuit for performing control of the system. The DSC 5 is composed of an A/D converter 13 for converting the reflected echo signal from the video signal processing circuit 4 into a digital signal, a plurality of pages of frame memories 14a, 14b, . . . , 14n for storing topographic image data digitalized in the A/D converter 13 in a time series, an ultrasonic transmission synchronizing circuit 15 for generating timing of writing tomographical image data in the frame memories 14a to 14n, a television synchronizing circuit 16 for generating a read timing in reading the tomographical image data out of the frame memories 14a to 14n and a controller 17 for controlling the operation of these elements. The controller 17 includes a CPU and a memory.

The subtracter 6 functions as a circuit for performing computation among tomographical images in a time series obtained with the DSC 5 to form differential image data thereof. It performs subtraction between two frames of tomographical image data read out under control of timing from the television synchronizing circuit 16, and is structured using a standard logic. Further, the image display unit 7 is for displaying differential image data outputted from the subtracter 6 as images, and consists of, for example, a D/A converter which converts the differential image data into analog signals and a television monitor which receives the converted video signals and displays them in colors.

In the present embodiment, the color code adding circuit 8 is provided on the output side of the DSC 5, the frame memories 9a to 9n and the color mapping circuit 10 are connected with the output side of the subtracter 6, and the controller 11 is further provided as shown in FIG. 2. The controller 11 includes a CPU and a memory therein. The color code adding circuit 8 functions as circuit for adding color codes for giving different hues to each pair of frames of tomographical image data outputted from the DSC 5 which processed with a differential operation, and adds one bit or a plurality of bits to the topographic image data which have been read out from respective frame memories 14a to 14n in the DSC 5 and writes color codes in the added bits. The number of the added bits may be 3 bits for coloring with eight colors and 4 bits for coloring with 16 colors.

The color code adding circuit 8 is provided between the frame memories 14a to 14n and the subtracter 6 in the present embodiment but is not limited thereto. The color code adding circuit 8 may be provided between the subtracter 6 and the frame memories 9a to 9n or between the frame memories 9a to 9n and the color mapping circuit 10. In the latter case, the color codes are added to differential image data of a pair of frames topographic image data.

A plurality of frame memories 9a, 9b, . . . 9n provided on the output side of the subtracter 6 store respectively differential image data formed by computation by the subtracter 6 from a plurality of frames of topographic image data corresponding to, for example, a one period portion of the moving tissue of the patient, and writing and reading respective image data are controlled by a controller 11 which will be described later. When topographic images $A_1, A_2, \ldots, A_n$ are taken into the frame memories 14a to 14n, differential images $P_1, P_2, \ldots, P_{N-1}$ which are obtained through $A_2 - A_1 = P_1$, $A_3 - A_2 = P_2, \ldots, A_N - A_{N-1} = P_{N-1}$ are stored in the frame memories 9a to 9n.

Further, the color mapping circuit 10 connected with the output side of these frame memories 9a to 9n performs required coloring in accordance with the value of a one bit color code flag added by the color code adding circuit 8 and also superposes a plurality of differential image data in reading the differential image data out of the respective frame memories 9a to 9n synchronously with a reading clock of the television synchronizing circuit 16.

Figure 3:
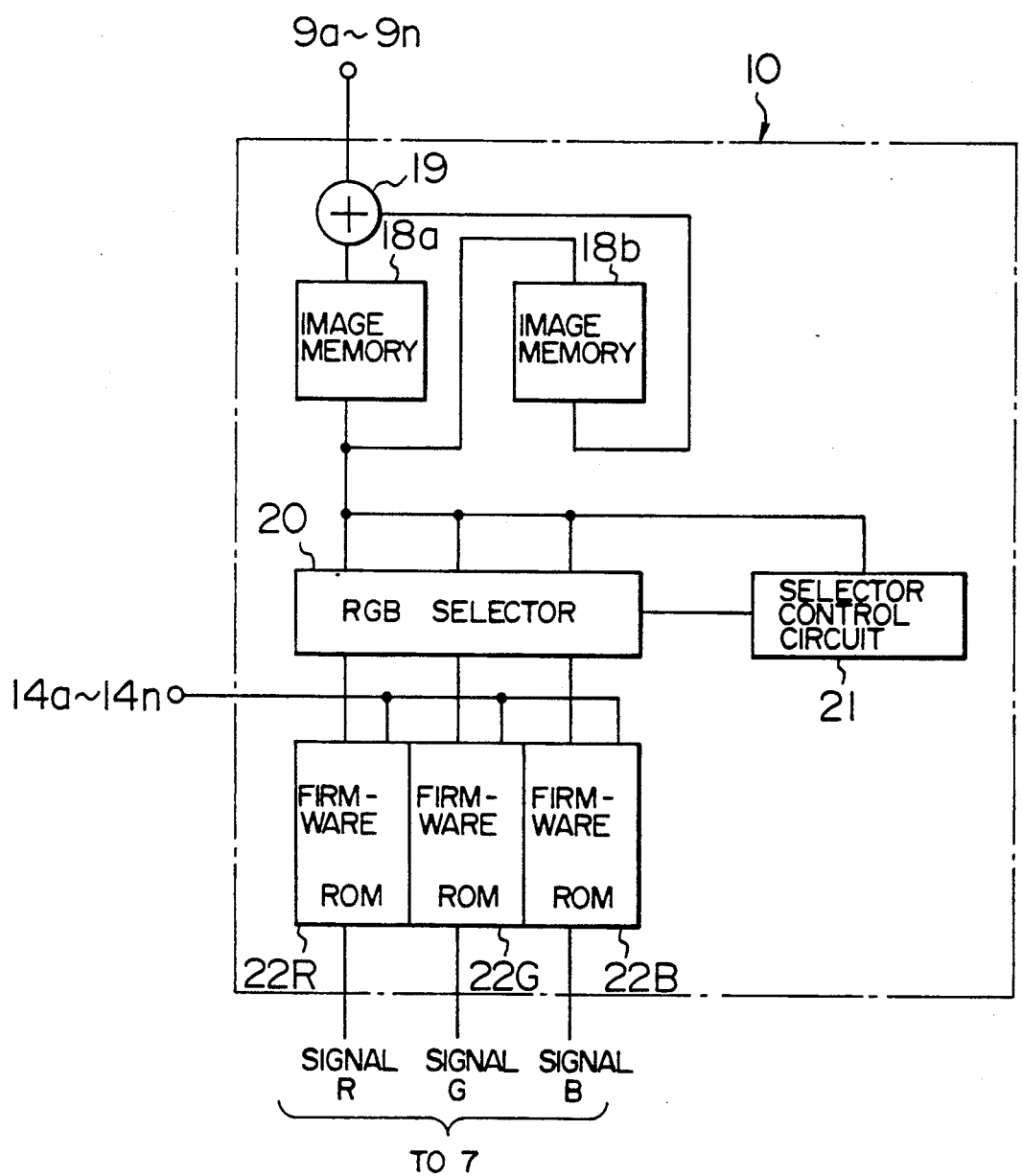
FIG. 3 is a block diagram of a color mapping circuit.

FIG. 3 shows an example of the color mapping circuit 10. Namely, the color mapping circuit 10 is composed of a first and a second image memories 18a and 18b for storing differential image data which have been read out from respective frame memories 9a to 9n shown in FIG. 2 in consecutive order, an adder 19 for adding image data from the second image memory 18b and differential image data from respective frame memories 9a to 9n together, an RGB selector 20 which receives the differential image data from the first image memory 18a and processes the output from RGB selector 20 and applies the result to any of firmware ROMs 22R, 22G and 22B which will be described later, a selector control circuit 21 which determines which of the firmware ROMs 22R, 22G and 22B the differential image data are to be outputted in accordance with color codes added to the differential image data from the first image memory 18a and sends out a change-over signal to the RGB selector 20, and firmware ROMs 22R (for red color), 22G (for green color) and 22B (for blue color) which converts the differential image data inputted through the RGB selector 20 into predetermined color signals and sends out the color signals to terminals R, G and B of the image display unit 7, respectively. Black and white tomographic image data from the frame memories 14a to 14n shown in FIG. 2 are inputted to other addresses of the firmware ROMs 22R, 22G and 22B. Further, these frame memories 9a to 9n and color mapping circuit 10 form a circuit for converting into colors designated by the color codes added with the color code adding circuit 8 with respect to the differential image data from the subtracter 6 and superposing a plurality of differential image data.

Furthermore, the controller 11 controls the operation in the color code adding circuit 8, the frame memories 9a to 9n and the color mapping circuit 10, respectively.

The operation of an ultrasonic diagnostic apparatus of the present invention as described above is described as follows. First, the probe 1 is abutted against a position corresponding to the portion of the patient's body to be diagnosed, and transmits an ultrasonic wave to the portion to be diagnosed. At this time, the ultrasonic wave transmitted from the probe 1 forms a fine beam in the portion of the patient's body to be diagnosed by means of a transmitting wave shaping circuit in the transmitting circuit 2. A reflected echo produced by the transmission beam striking against the portion to be diagnosed and reflected therefrom is received by the probe 1, and a reception beam is formed in a received beam phasing circuit in the receiving circuit 3. Then, transmission and reception of the ultrasonic wave are repeated to and from the probe 1 by varying the transmitting-receiving directions of the ultrasonic wave with a predetermined period consecutively in order to scan the portion of the patient's body to be diagnosed.

The reception beam outputted from the receiving circuit 3 is transmitted to the DSC 5 as a reflected echo signal after being processed with required signal processing in the video signal processing circuit 4 and is inputted to the A/D converter 13 to be converted into a digital signal. The DSC 5 has a plurality of line memories (not shown) with which reading and writing are performed under the control of the controller 17 every time the ultrasonic transmitting-receiving direction is varied, and a digital reflected echo signal is sent to the frame memories 14a to 14n for each reception beam inputted consecutively in order. The reflected echo signal inputted to these frame memories 14a to 14n is written in the frame memory 14a in a first image storage area by means of the control signal of the controller 17 as one frames of a tomographic image data while having the transmitting-receiving direction thereof correspond to each ultrasonic beam, thus forming a first image.

When ultrasonic scanning of one frame of tomographic image portion is thus completed, the probe 1 returns the transmitting-receiving direction to an initial direction again by the control of the transmitting circuit 2 and the receiving circuit 3 and repeats transmitting-receiving of an ultrasonic wave by renewing the transmitting-receiving direction to the initial direction. Then, the reflected echo signal collected at this time is also processed with A/D conversion as described above and sent to the frame memories 14a to 14n, and is written in the frame memory 14b in a second image storage area by the control of the controller 17 as one frame of tomographic image to form a second image. Third to nth images are formed similarly to the foregoing.

Then, when the first image and the second image are formed as described, the first image and the second image are read out of the frame memories 14a and 14b while having mutual picture elements thereof correspond to each other by the control of the controller 17, respectively. This pair of images are inputted to the color code adding circuit 8. Then, the color code adding circuit 8 adds a plurality of bits to the read out pair of images and writes color codes in these added bits. The number of added bits may be determined to be two bits corresponding to three terminals R, G and B of the image display unit 7. Further, it is possible to form differential images as images in different colors for every frame or every several frames by changing color codes for every frame or after several frames are read out from the frame memories 14a to 14n. In this case, when it is assumed that the number of colors which can be displayed by the ultrasonic diagnostic apparatus is n, the color initialization may be set, for example, from the first color to the nth color in consecutive order. If an operator may set the order of colors and the number of consecutive frames between which colors are changed from a console (not shown) and the order of setting colors is stored in the controller 11, it is possible to obtain an image colored in the same order of colors however many times the tomographic images are taken.

Figure 4:
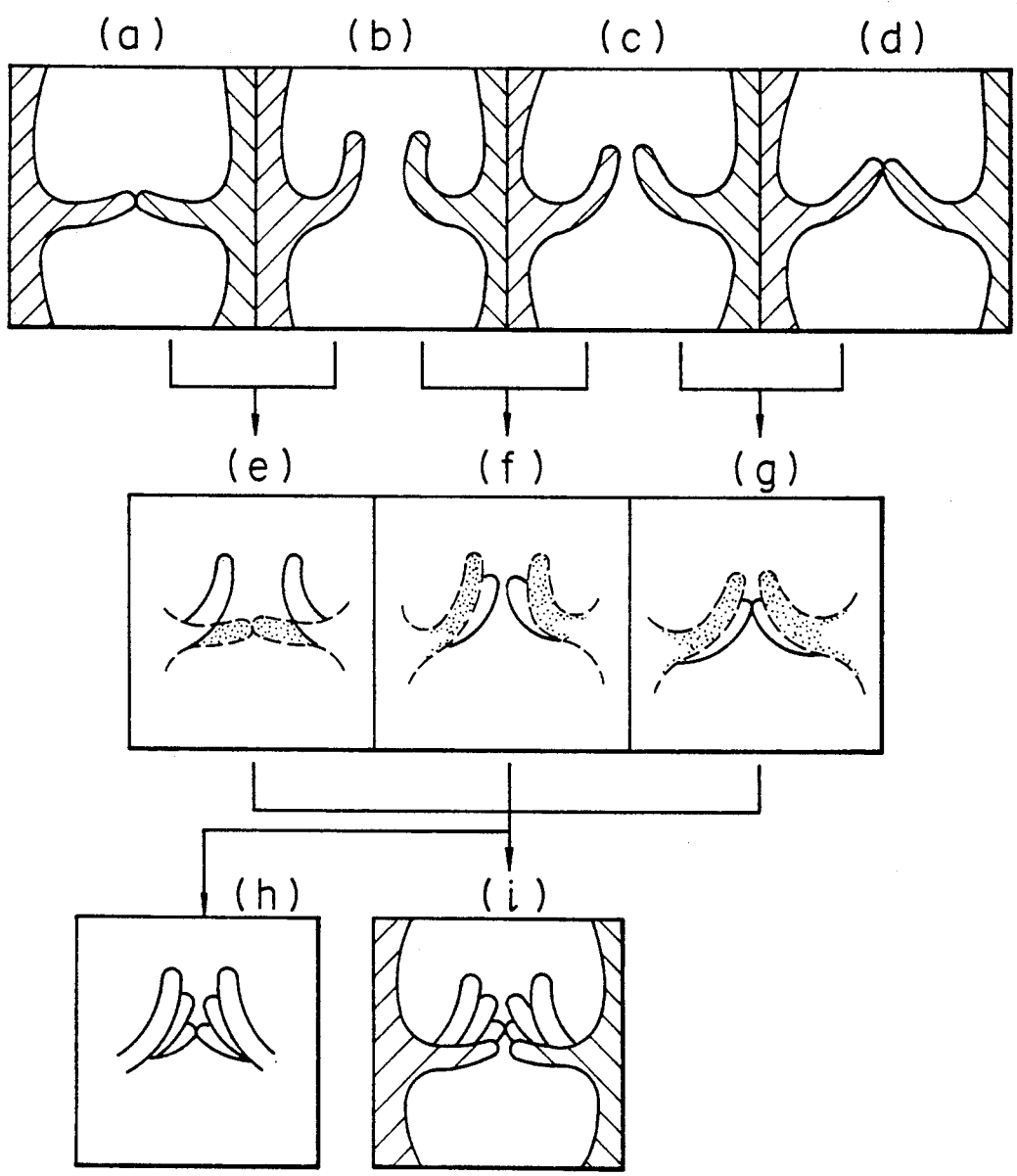
FIG. 4 is an explanatory diagram showing an example of display operation by superposing of differential images in the first embodiment.

The data of the first image (FIG. 4 (a)) and the second image (FIG. 4 (b)) are sent to the subtracter 6 in this state, respectively. Then, the subtracter 6 performs subtraction for every corresponding picture element in the first and second images, and outputs differential data (FIG. 4 (e)) between the first image and the second image successively. Further, the differential data of respective picture elements outputted from the subtracter 6 are inputted and stored in one of the frame memories 9a to 9n at the next stage. Thereafter, the differential image data are read out of these frame memories 9a to 9n synchronously with the 5 read clock of the television synchronizing circuit 16, and are sent to the color mapping circuit 10.

The differential image data inputted to the color mapping circuit 10 are written into a first image memory 18a through adder 19 in FIG. 3. Next, the differential image data with color codes added is read out of the first image memory 18a and the data portion of the differential images is inputted to the RGB selector 20, and the color codes are inputted to the selector control circuit 21. Then, the selector control circuit 21 determines the firmware ROM 22R, 22G or 22B to which the differential image data is outputted in accordance with the inputted color codes and sends a required change-over signal to the RGB selector 20. For example, when the inputted color code specifies "red", the selector control circuit 21 outputs a change-over signal for changing over the RGB selector 20 so as to send the differential image data to the firmware ROM 22 for red color. Then, the RGB selector 20 selects the firmware ROM 22R with the change-over signal, and the inputted differential image data are inputted to the firmware ROM 22R for red color. As a result, the differential image data are converted to red color by means of the firmware ROM 22R, and sent out to the image display unit 7 as the R signal so as to be displayed in color.

If superposition of the differential image data is designated at this time, synchronously with readout of the differential image data in the first frame for instance from the first image memory 18a, the readout differential image data in the first frame are written in a second image memory 18b. Next, the differential image data in the second frame are read out of the second frame memory 9b and sent to the color mapping circuit 10 so as to be inputted to the adder 19. At the same time, the differential image data in the first frame which have been stored previously are read out from the second image memory 18b and sent to the adder 19. Then, the adder 19 adds the inputted differential image data of the first frame to the differential image data from the second frame and sends the addition result to the first image memory 18a. As a result, the differential image data in the first frame and the differential image data in the second frame are superposed in the first image memory 18a and stored on one page of image memory.

Next, superposed differential image data in the first frame and the second frame are read out of the first image memory 18a in this state. Then, the data portion of the differential image is inputted to the RGB selector 20 in the similar manner as the foregoing, the portion of the color code is inputted to the selector control circuit 21, and the RGB selector 20 is changed over in accordance with respective color codes of superposed images. With this, the image data are inputted to the firmware ROMs 22R, 22G and 22B and converted into required colors, and are outputted to the image display unit 7 so as to be displayed in colors.

Next, synchronously with readout of the differential image data in which the first frame and the second frame are superposed from the first image memory 18a, the read out differential image data in the first sheet and the second sheet are written in the second image memory 18b. When the differential image data, for example, the differential image data in the third sheet are read out of the third frame memory 9c and inputted to the adder 19 of the color mapping circuit 10 thereafter, the superposed differential image data in the first frame and the second frame are read out of the second image memory 18b and added to the inputted differential image data in the third frame by the adder 19. The result of addition is sent to the first image memory 18a, and the differential image data in the first frame, the second frame and the third frame are superposed in the first image memory 18a and stored on the image memory in one frame. It is possible to superpose differential images in an optional number of frames in one frame of image in consecutive order and to apply required coloring to respective differential images so as to display in colors on the image display unit 7 by repeating the above-described operation thereafter.

At this time, as to the differential images inputted from the frame memories 9a to 9n, the order of coloring the differential images may be displayed in rainbow colors as red, orange, yellow, green, blue, indigo and violet in succession from the differential image in the first frame, or may be displayed by coloring a warm color system and a cool color system alternately in such an order as red, violet, orange, indigo, yellow and blue in case of small displacement among respective differential images. It is possible to superpose black and white original tomographic images so as to display the background for thus colored differential images by inputting original tomographic image data before being applied with the above-described operation processing which have been read out of the frame memories 14a to 14n to other addresses of respective firmware ROMs 22R, 22G and 22B of the color mapping circuit 10 shown in FIG. 3.

Next, the display operation of the differential images by giving hues and superposing as described above will be described with reference to FIG. 4. FIG. 4 shows displaying the movement of a valve of a heart with differential processing as an example. Parts (a) to (d) in FIG. 4 show tomographic images stored in a time series in the frame memories 14a to 14n, (e) to (g) in FIG. 4 show differential images obtained by differential operation between the adjacent tomographic images and stored in other frame memories 9a to 9n, and FIG. 4 (h) shows a differential image obtained by superposing the above-described respective differential images. Namely, the differential image in the first frame shown in FIG. 4 (e) is obtained by performing differential operation with the subtracter 6 between the first image (a) stored in the frame memory 14a and the second image (b) stored in the frame memory 14b. Further, the differential image in the second frame shown in FIG. 4(f) is obtained by performing differential operation between the second image (b) stored in the frame memory 14b and the third image (c) stored in the frame memory 14c (not shown). Furthermore, the differential image in the third frame shown in FIG. 4 (g) is obtained by performing a differential operation between the third image (c) stored in the frame memory 14c and the fourth image (d) stored in the frame memory 14d (not shown). Here, in the differential image shown in (e) to (g) in FIG. 4, the void portions show portions where positive values have remained as the result of above-described differential operation, and the portions which look black show portions where negative values have remained.

Three frames of differential images are superposed as a one frame image as shown in FIG. 4 (h) by adding data of three frames of differential images (e), (f) and (g) as for instance obtained as described above in consecutive order by means of the first and the second image memories 18a and 18b and the adder 19 of the color mapping circuit 10 shown in FIG. 3. In FIG. 4 (h), superposing has been made leaving only positive values in respective differential images (e), (f) and (g) is shown. However, it is possible not to display negative values in respective differential images (e), (f) and (g) by controlling the addresses of the firmware ROMs 72R, 22G and 22B in the color mapping circuit 10 by means of the controller 11 shown in FIG. 2 and converting differential image data having negative values into a value equal to that of the background.

Furthermore, when it is desired to use an original tomographic image (for example, the first image shown in FIG. 4 (a)) as a background image as shown with hatched lines in FIG. 4 (i), it is only required to control the frame memories 14a to 14n from the controller 17, to read tomographic image data desired as the background image, and to input these data to other addresses of the firmware ROMs 22R, 22G and 22B shown in FIG. 3.

By displaying (N−1) frames of differential images by superposing for N frames of tomographic images as described above, those portions that have moved from the time of the first image acquisition to the time of the Nth image acquisition are displayed.

Further, when differential image data are obtained in consecutive order by performing subtraction among adjacent images one after another and are displayed continuously on the image display unit 7, real time images of only the moving tissue of the portion of the patient's body to be diagnosed are obtained. At this time, it is necessary to take the velocity of the moving tissue into consideration with respect to the frame rate of the display of the image display unit 7. In order to obtain differential images of moving tissue which is higher than the standard frame rate of the image on the image display unit 7, it is recommendable to use the technique described in U.S. Pat. No. 4,254,662 for ultrasonic transmit-receive techniques.

When the moving velocity of the tissue of a patient to be diagnosed is not so high as compared with the ultrasonic transmission period, the variation of the obtainable differential images is small (difference among differential images is small), and it sometimes happens that the variation quantity cannot be displayed if those differential images are superposed. In such a case, it is only required to widen the space between differential images which are outputted after operation by skipping reading of the frame memories 14a to 14n at spaces of several frames for the tomographic image data which are outputted from the DSC 5 when differential images are formed with the subtracter 6.

Further, in the above-described embodiment a different hue is given to each image of the differential images. However, the embodiment is not limited thereto. In the case of a body part moving slowly or in case when the movement of an organ is difficult to discriminate with differential images, viz., the frame rate is not matched, an optional number of sheets of differential images are made in one set and different hue is given to each set. Differential images in which the sequence of respective sets corresponds to one another are read and superposed for display.

Figure 5:
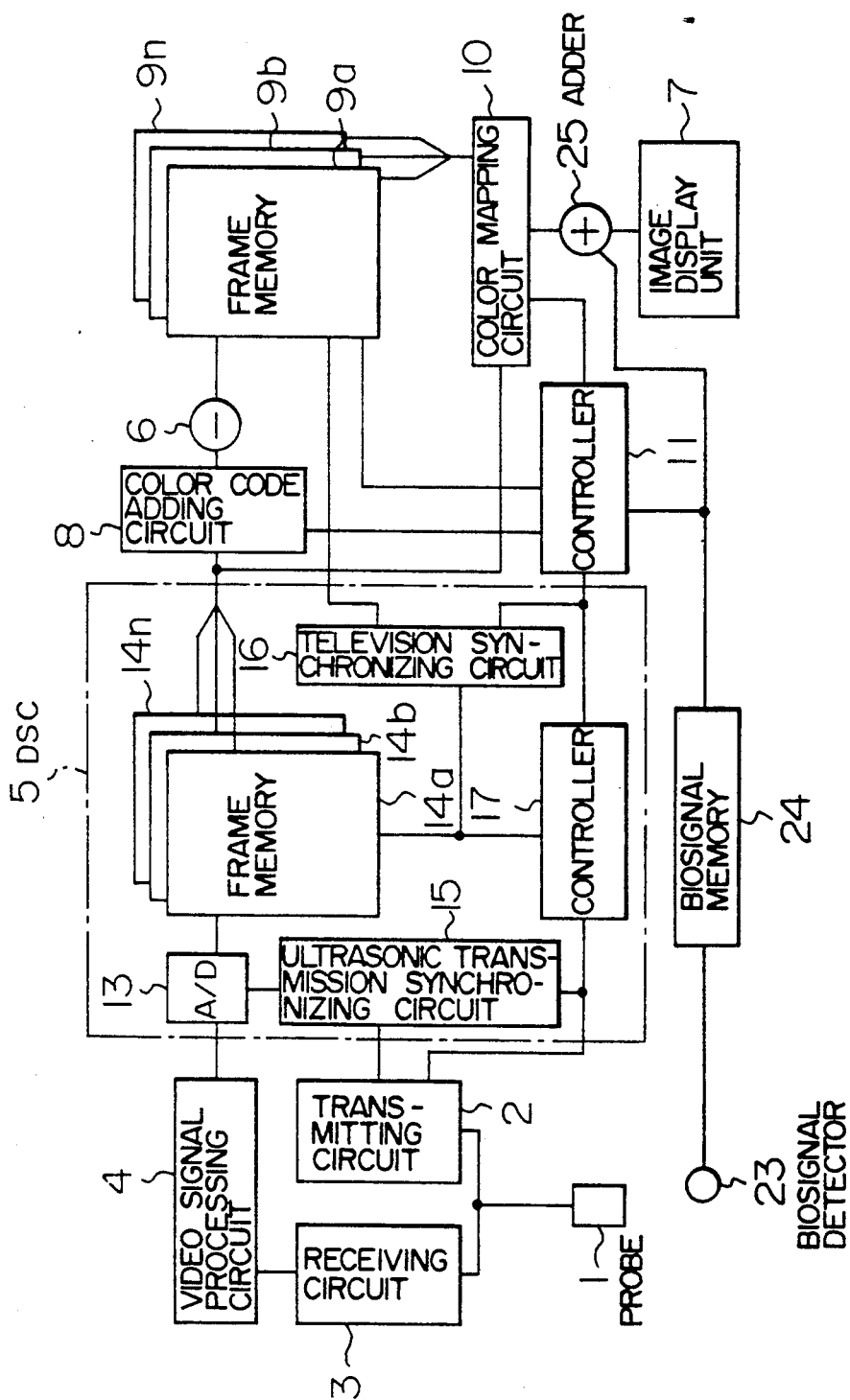
FIG. 5 is a block diagram showing a second embodiment of the present invention.

FIG. 5 is a block diagram showing a second embodiment of the present invention. In the present embodiment, a biosignal detector 23, a biosignal memory 24 and an adder 25 are added to the embodiment shown in FIG. 2, and output data from the adder 25 are inputted to the image display unit 7. The biosignal detector 23 detects biosignals with respect to a patient's body and is composed of an electrocardiograph, an phonoelectrocardioscope or the like attached to the limbs and the like of the patient and detects biosignals such as an electrocardiogram, a phonoelectrocardiogram and a pulse wave, and outputs the waveform data thereof. Further, the biosignal memory 24 writes and reads the biosignal data detected by the biosignal detector 23 synchronously with the tomographic data of the DSC 5, and is controlled by means of the controller 17 and another controller 11. Further, it is possible to read tomographic image data which correspond one to one to respective parts of the biosignal data out of the DSC 5 using the biosignal data of the biosignal memory 24, and also to display differential images which correspond to respective parts of the designated biosignal with a marker 26 as in FIG. 6 by adding color codes in the color code adding circuit 8 and changing the color for each frame. Furthermore, the adder 25 adds the differential image data having coloring applied with the color mapping circuit 10 to biosignal data such as an electrocardiogram outputted from the biosignal memory 24 so as to display on the image display unit 7 at the same time.

The operation of a special portion of the second embodiment will be described hereinafter. First, simultaneously with reception of one frame of tomographic data by the DSC 5, an electrocardiogram from a patient is detected by the biosignal detector 23, and the data from the electrocardiogram is stored in the biosignal memory 24. At this time, the electrocardiographic data are written in the biosignal memory 24 synchronously with the ultrasonic transmission synchronizing circuit 15 and read out synchronously with the television synchronizing circuit 16 in a similar manner as reading and writing of tomographic image data from and to the frame memories 14a to 14n. With this, respective parts of tomographic data stored in the frame memories 14a to 14n and electrocardiographic data stored in the biosignal memory 24 correspond to one another one to one. Thus, it is possible to specify and designate tomographic image data stored in the frame memories 14a to 14n by designating the electrocardiographic data to the biosignal memory 24. With this, tomographic data are designated by designating one point of the electrocardiographic data with a marker, and differential image data formed by differential operation synchronized with the electrocardiographic data.

By designating a specific electrocardiogram through operation of a console (not shown) while monitoring an electrocardiogram displayed together with differential images of the patient's body on the scope of the image display unit 7 through the adder 25 shown in FIG. 5, the differential image data stored in other frame memories 9a to 9n can be designated. By adding a required color code with the color code adding circuit 8 through the controller 11, coloring can be designated for each frame of the differential images.

Figure 6:
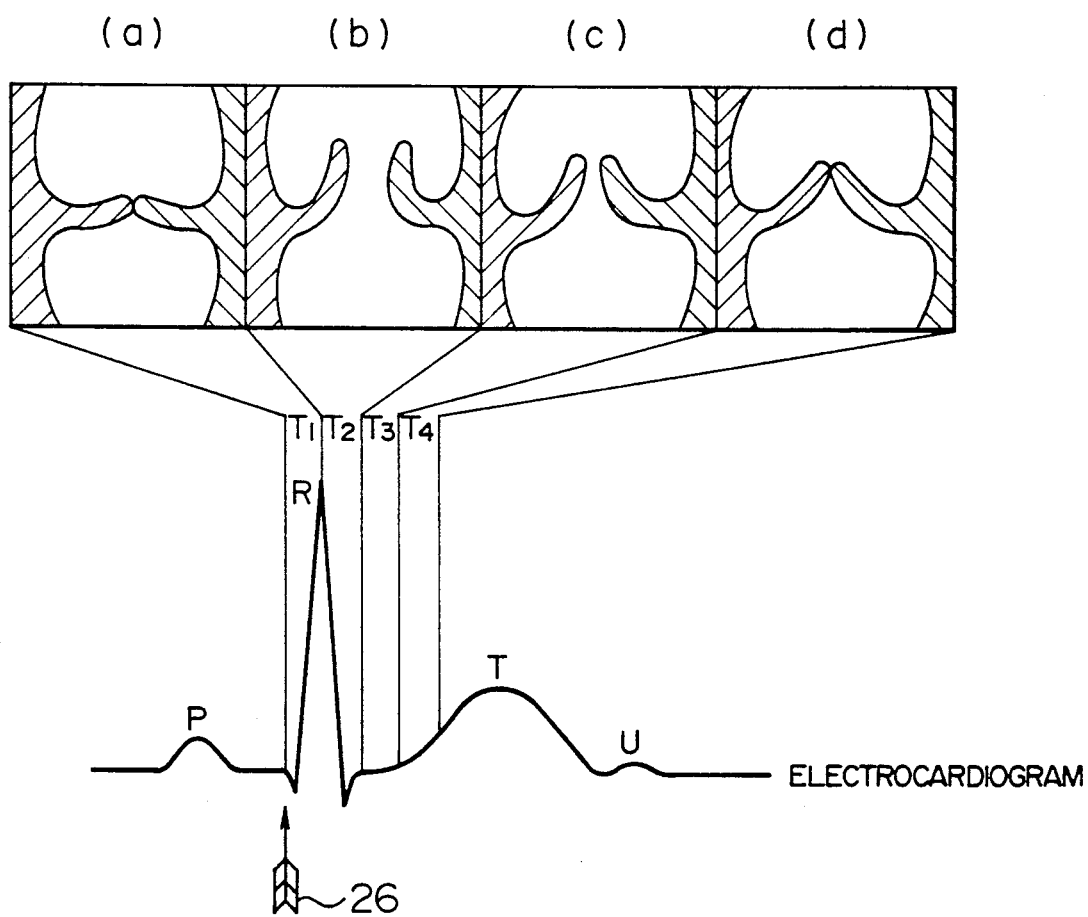
FIG. 6 is an explanatory diagram showing a example of display operation of differential images by designation of electrocardiogram in the second embodiment.

The operation of displaying differential images by designation of the electrocardiogram will be described with reference to FIG. 6. FIG. 6 shows an electrocardiogram detected from a patient and tomographic images stored in the frame memories 14a to 14n. In FIG. 6, the tomographic images shown in (a) to (d) are obtained by collecting data at the timing T1, T2, T3 and T4 on the electrocardiogram, respectively, in which respective portions of electrocardiographic data and the tomographic image data correspond one to one to one another. Further, differential images obtained by differential processing of tomographic images shown in (a) and (b), (b) and (c), and (c) and (d) are as shown in (e), (f) and (g) in FIG. 4, respectively. Further, due to the fact that the tomographic image data and the electrocardiographic data correspond one to one to one another, the differential image data obtained as described above also correspond one to one to respective parts of the electrocardiographic data. Thus, it is possible to designate the differential images to which (e) to (g) in FIG. 4 correspond by designating the timing $T_1$ to $T_4$ on the electrocardiogram by moving the marker 26 while monitoring the electrocardiogram displayed on the scope of the image display unit 7 shown in FIG. 5. Then, it becomes possible to apply coloring to the differential images in each frame by designating coloring on the designated differential images.

For example, when the timing $T_1$ on the electrocardiogram is designated first by operating the marker 26, the differential image shown in FIG. 4 (e) is selected and for example it is designated to color this differential image in red color. Next, when the timing $T_2$ is designated by operating the marker 26, the differential image shown in FIG. 4 (f) is selected, and it is designated for example to color this differential image in blue color. Furthermore, when the timing $T_3$ is designated also by operating the marker 26, the differential image shown in FIG. 4 (g) is selected, and it is for example designated to color this differential image in green color. In such a manner, it is possible to color the differential images in each frame in the frame memories 9a to 9n. In this case, by performing coloring designation on respective differential images using one period of a portion of a heartbeat recorded by an electrocardiogram, and preserving the electrocardiogram designated for coloring, coloring designation may not be made again on the differential data obtained therefrom even when tomographical data are collected again.

FIG. 6 is a block diagram of a third embodiment in which weighing coefficients are given to respective differential images to make it possible 25 to display the magnitude and the direction of the velocity of a moving part of the patient's body being diagnosed.

Figure 7:
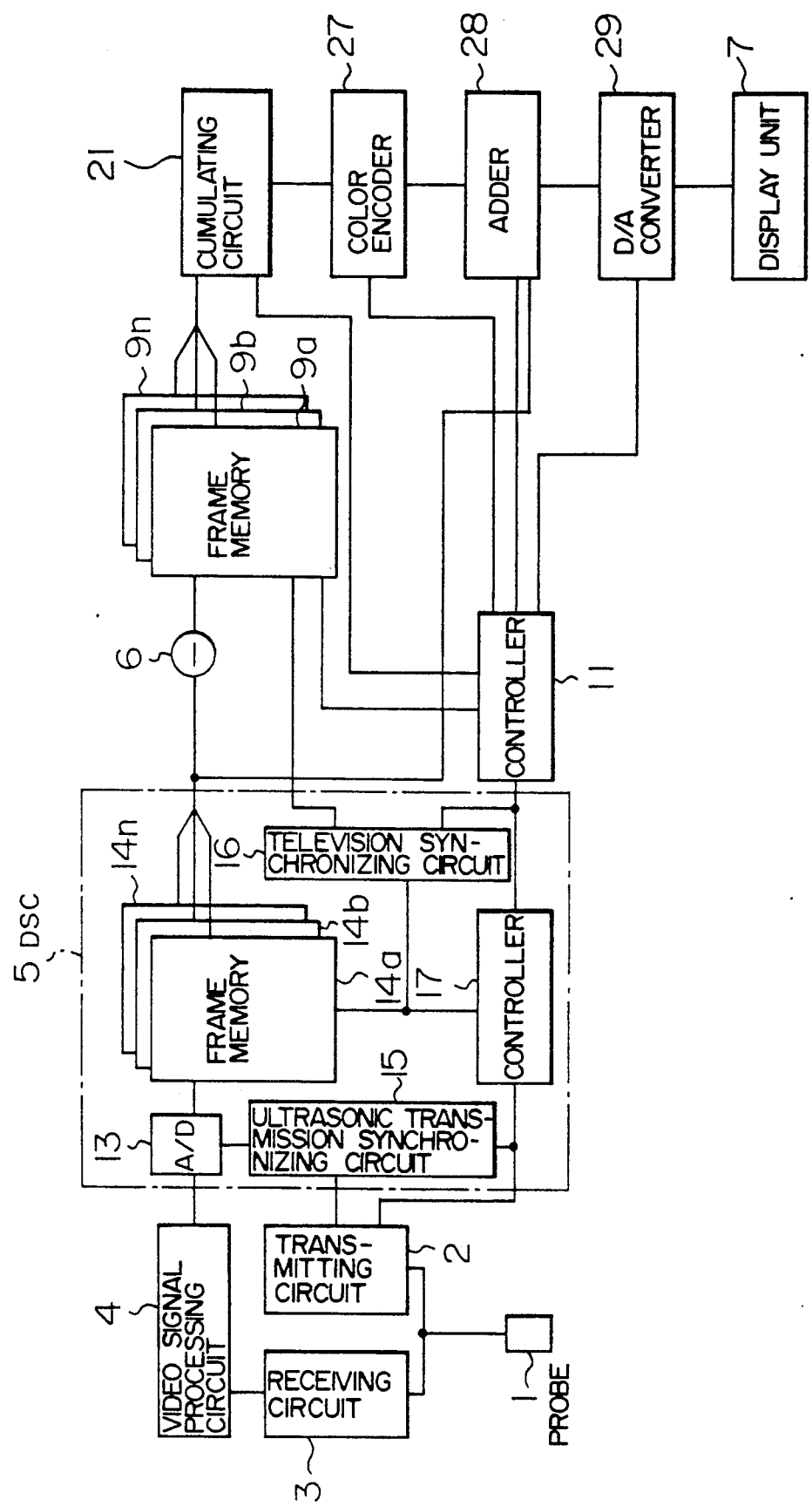
FIG. 7 is a block diagram for explaining a third embodiment according to the present invention.

In FIG. 7, the structure after the frame memories 9a–9n is different from that shown in FIG. 2. A color encoder 27 allocates a display color which is different depending on the luminance level. An adder 2 displays colored cumulative differential images and black and white tomographic images read out of the frame memories 14a to 14n by superposing them. The output of he adder 28 is converted into an analog signal by a D/A converter 29 and inputted to the image display unit 7.

Figure 8:
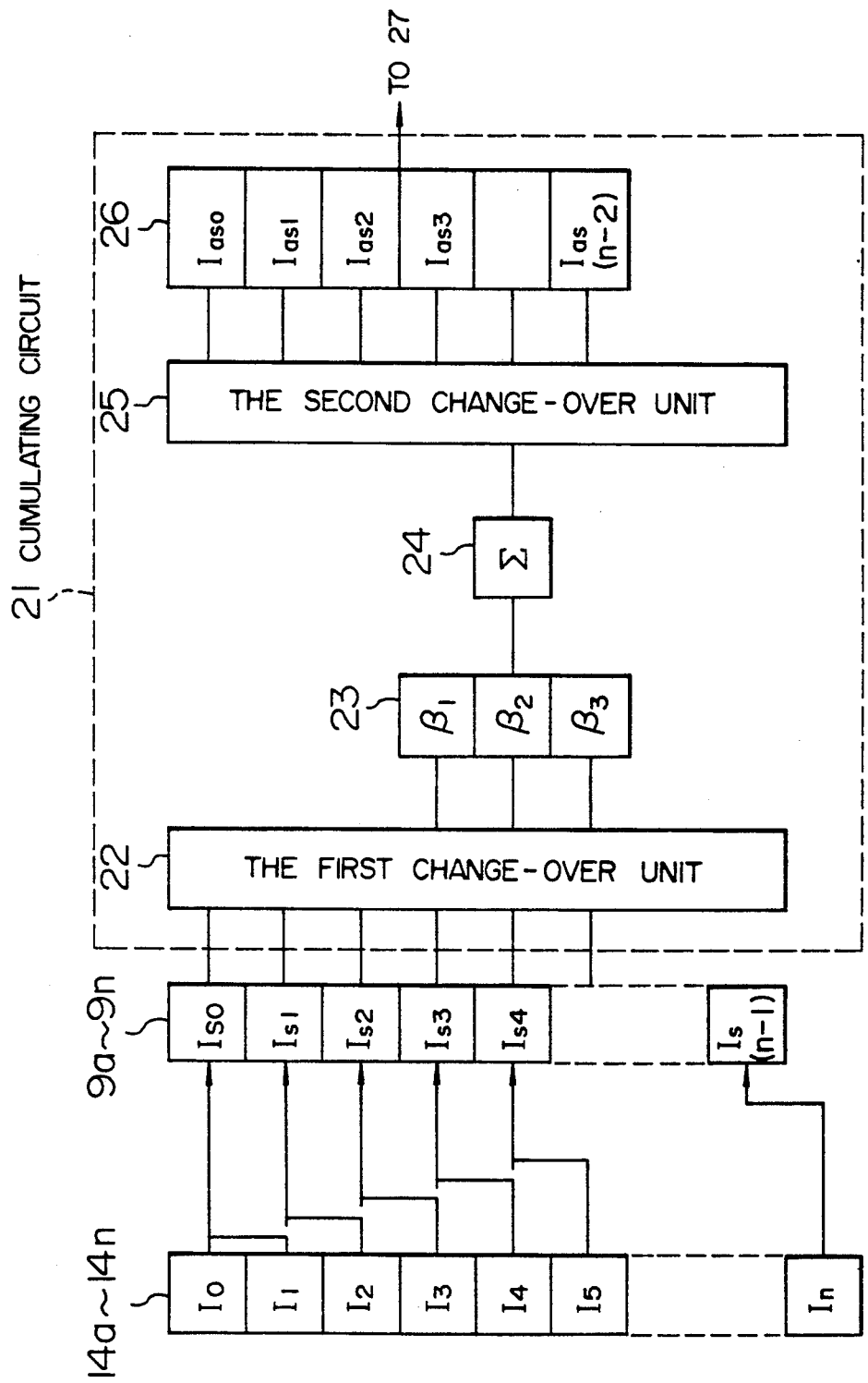
FIG. 8 is a diagram of a cumulating circuit.

FIG. 8 is a detailed diagram of a cumulative processing circuit 21 shown in FIG. 7. As described already relating to FIG. 2, differential images $I_S0$ to $I_{S(n-1)}$ are stored in the frame memories 9a to 9n from tomographic images $I_0$ to $I_n$ taken into the frame memories 14a to 14n. For example, three differential frames of image data are selected in a time series from the frame memories $9a$ to $9n$ by means of a first change-over unit 22 and inputted to a multiplier 23, and are weighted by being multiplied by predetermined weighing coefficients $\beta_1$, $\beta_2$, and $\beta_3$. Three differential images weighted by a summer 24 are applied with cumulative processing, and the result thereof is stored in an image memory 26 by means of a second change-over unit 25.

Namely, cumulative differential images $I_{aS0}$, $I_{aS1}$, $I_{aS(n-2)}$, are obtained by the following operation.

$$I_{S0}\cdot\beta_1 + I_{S1}\cdot\beta_2 + I_{S2}\cdot\beta_3 = I_{aS0}$$

$$I_{S1}\cdot\beta_1 + I_{S2}\cdot\beta_2 + I_{S3}\cdot\beta_3 = I_{aS1}$$

$$I_{S(n-3)}\cdot\beta_1 + I_{S(n-2)}\cdot\beta_3 + I_{S(n-1)}\cdot\beta_3 = I_{aS(n-2)}$$

The details of the third embodiment of the present invention are shown in FIGS. 9 through 12. In the present embodiment, offset is applied to the tomographic image data in obtaining the differential images so as to make it possible to display the magnitude and the direction of the velocity of a moving portion.

Figure 9:
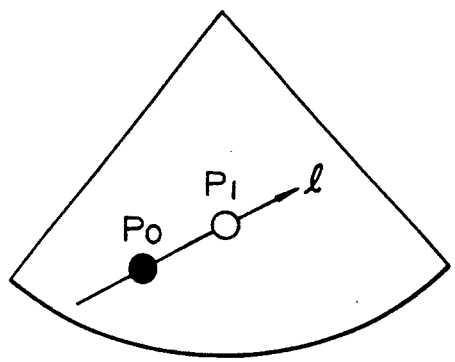
FIG. 9 is a diagram of a differential image.
Figure 10:
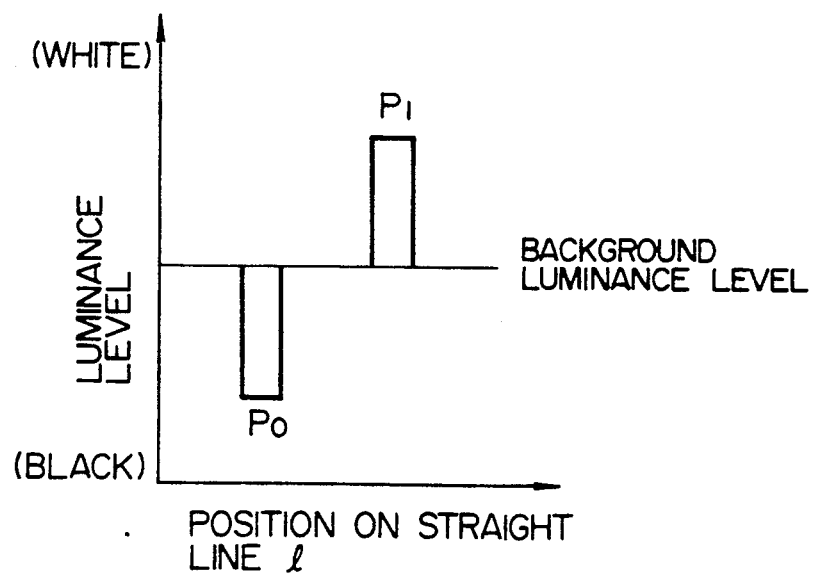
FIG. 10 is a diagram showing variation of a luminance level of a differential image.

FIG. 9 shows an example of a differential image, which is the differential image when the moving portion moved on a straight line 1 from a position $P_0$ to a position $P_1$. At this time, the differential value of a stationary portion becomes "zero" by subtracting a timewise old image from a timewise new image. Further, as to the moving portion, the luminance of the data on the new image side is displayed in white since the data remain as "positive", and the luminance of the data on the old image side is displayed in black since the data become "negative". Namely, when the abscissa shows the position on the straight line shown in FIG. 9 and the ordinate shows the luminance level of the image as shown in FIG. 10, the luminance at the point $P_1$ is displayed in the white direction and the luminance at the point $P_0$ is displayed in the black direction with the luminance level of the background (stationary portion) of the image (hereinafter referred to as the "background luminance level") as the reference.

Figure 11:
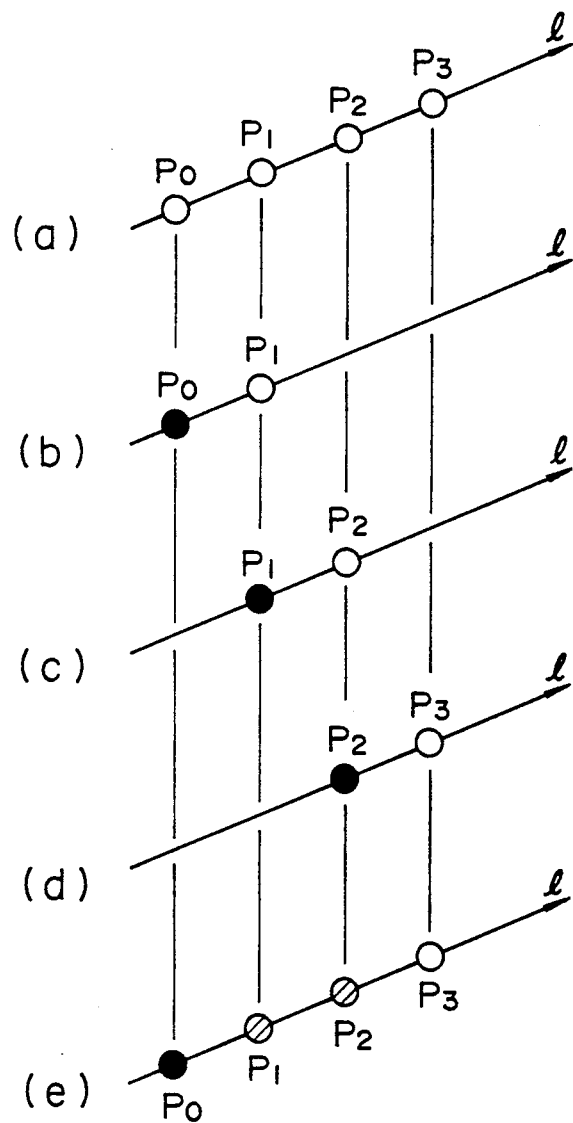
FIG. 11 is an explanatory diagram showing motion of a moving portion of a patient in a straight line as time elapses.
Figure 12:
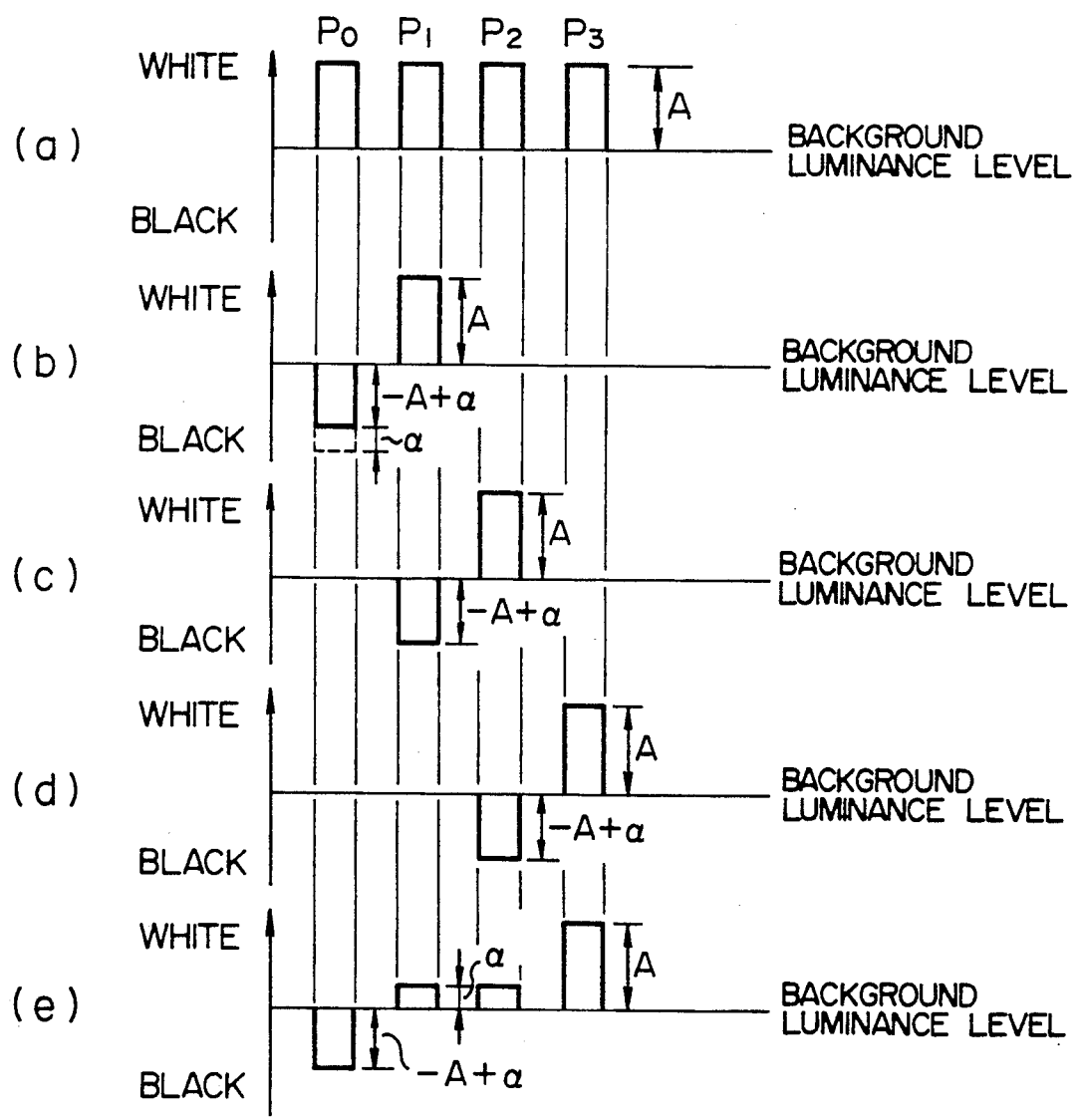
FIG. 12 is a diagram showing variation of a luminance level at respective positions of FIG. 11.

FIG. 12 shows luminance levels of respective images which are inputted to the frame memories $14a$ to $14n$ when the moving portion moves as time elapses from $P_0$ to $P_3$ as shown in FIG. 11(a). FIG. 12 shows in a similar manner as FIG. 10. The luminance levels for respective frames after movement of a moving portion P are shown in white which is of higher luminance than the background luminance level. In a conventional ultrasonic diagnostic apparatus, the change in the luminance level of a moving portion in each image has been observed visually to confirm by afterimage effect that it is moving in the direction of the straight line 1. On the contrary, the magnitude and the direction of the velocity of the moving portion is displayed on the scope by performing the following processing in the present invention. Here, (b) to (d) in FIG. 11 show respective differential images in a time series, and (b) to (d) in FIG. 12 show luminance levels corresponding to respective images. When cumulative processing of optional plurality of images (three frames of images in this case) is performed by means of the cumulating circuit 21 shown in FIG. 7, the luminance level appears as shown in FIG. 12(e). In this case, when a luminance level A at the point $P_0$ is subtracted from the luminance level A at the point $P_1$ as shown in FIG. 12(b), the differential data disappear in the cumulative image thereafter if subtraction is made. Therefore, the luminance level of the subtracting side is made to be $-A+\alpha$ ($\alpha$ is an offset). Thus, the luminance levels of cumulative differential image obtained from three sheets of differential images become A and $-A+\alpha$ corresponding to positions $P_3$ and $P_0$ and both show $+\alpha$ for intermediate points $P_2$ and $P_1$ as shown in FIG. 12(e). Thus, the cumulative differential image shows a white level at the position $P_3$ at one end and a luminance level close to a black level at the position $P_0$ at another end, and the luminance levels at intermediate positions $P_2$ and $P_1$ show values close to the background luminance level. Accordingly, it becomes possible for an observer to know the direction (vector) of a moving portion with one frame of cumulative differential image shown in FIG. 11(e).

In the above-described description, respective differential images have been cumulated with equal weighing as shown (b) to (d) in FIG. 12, but an embodiment in which respective differential images are cumulated with optional different weighing given thereto is shown in the next place. In this case, the weighted cumulative differential image data $I_{aS0}$ to $I_{aS(n-2)}$ are also read out of the cumulative differential image memory 26 and sent out to the color encoder 9, thus performing color encoding of the luminance level.

Figure 13:
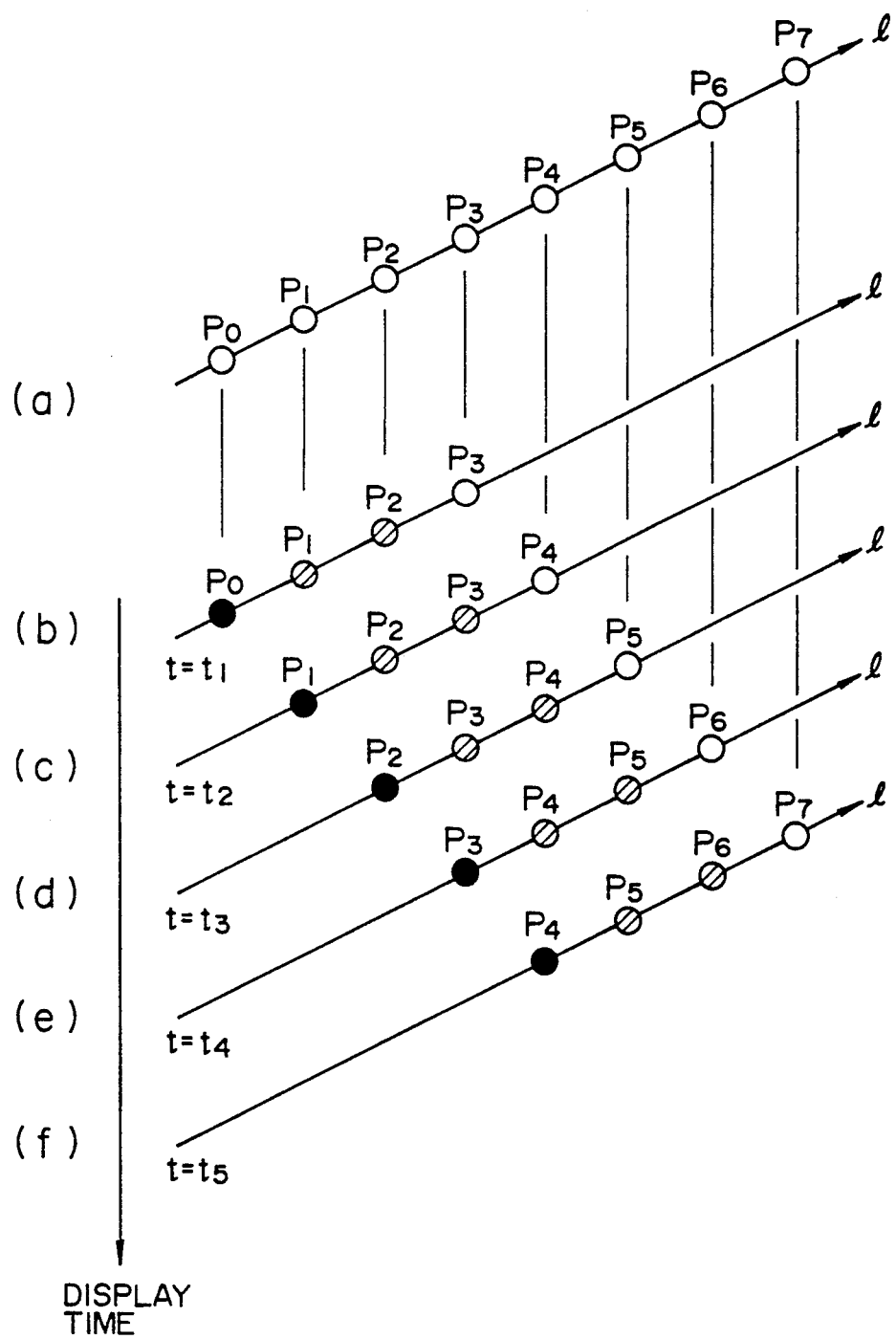
FIG. 13 is a diagram showing differential images given different weighing coefficients an cumulative differential images as displayed successively in a time series.

In such a manner, a cumulated differential image is obtained as shown in FIG. 11(e) by the cumulative processing circuit 21. Since the cumulative processing is executed successively in a time series, the cumulative differential image changes from (b) to (f) in FIG. 13 as the time changes from $t=t_1$ to $t=t_5$ as shown in FIG. 13. As a result, each of the cumulative differential images is displayed in a different color.

Therefore, it is possible to display an image of a velocity vector (magnitude and direction of velocity) of a moving portion of a patient's body, for example, to make dynamic observation for example of a bloodstream in real time easily. Thus, it is possible to improve diagnostic capability of an ultrasonic diagnostic apparatus to increase the clinical value.

Next, a fourth embodiment of the present invention will be described. In the fourth embodiment, the velocity vector display by the third embodiment is made continuously.

Figure 14:
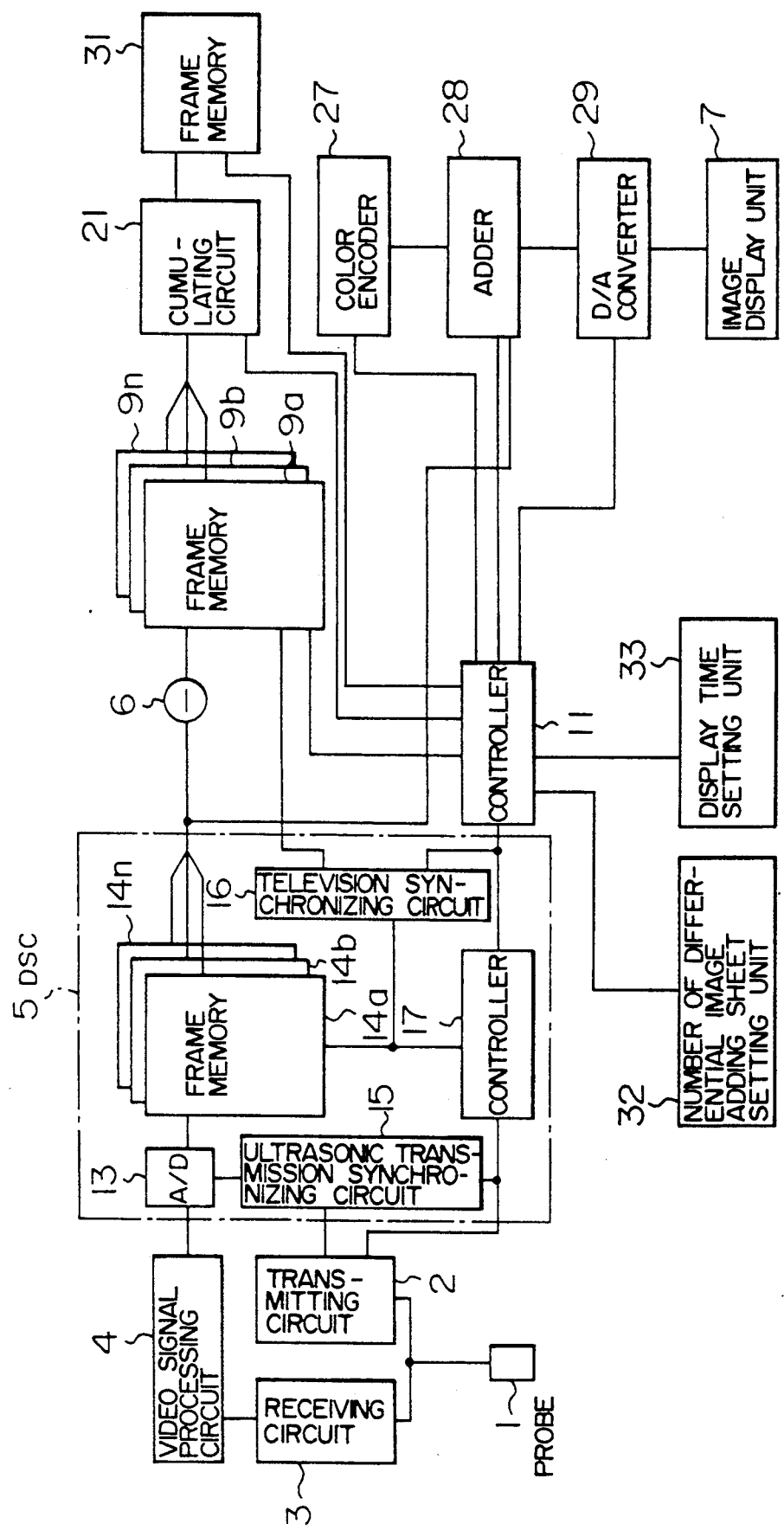
FIG. 14 is a block diagram explaining a fourth embodiment according to the present invention.

FIG. 14 shows the construction shown in FIG. 7 modified so that addition of differential images is made for every designated number of frames and these added differential images are cumulated.

In FIG. 14, 32 denotes a differential image addition number of frames setting unit, which outputs a plurality of frames of differential images stored in the frame memories $9a$ to $9n$ to the cumulative processing circuit 21 by the number of frames in which differential images have been set successively. Frame memory 31 stores cumulative differential images which are cumulated in the cumulative processing circuit 21 and are given hue information by the color encoder 9, and consists of for example a plurality of frame memories so that a plurality of frames of cumulative differential images which are separated in time may be stored.

Figure 15:
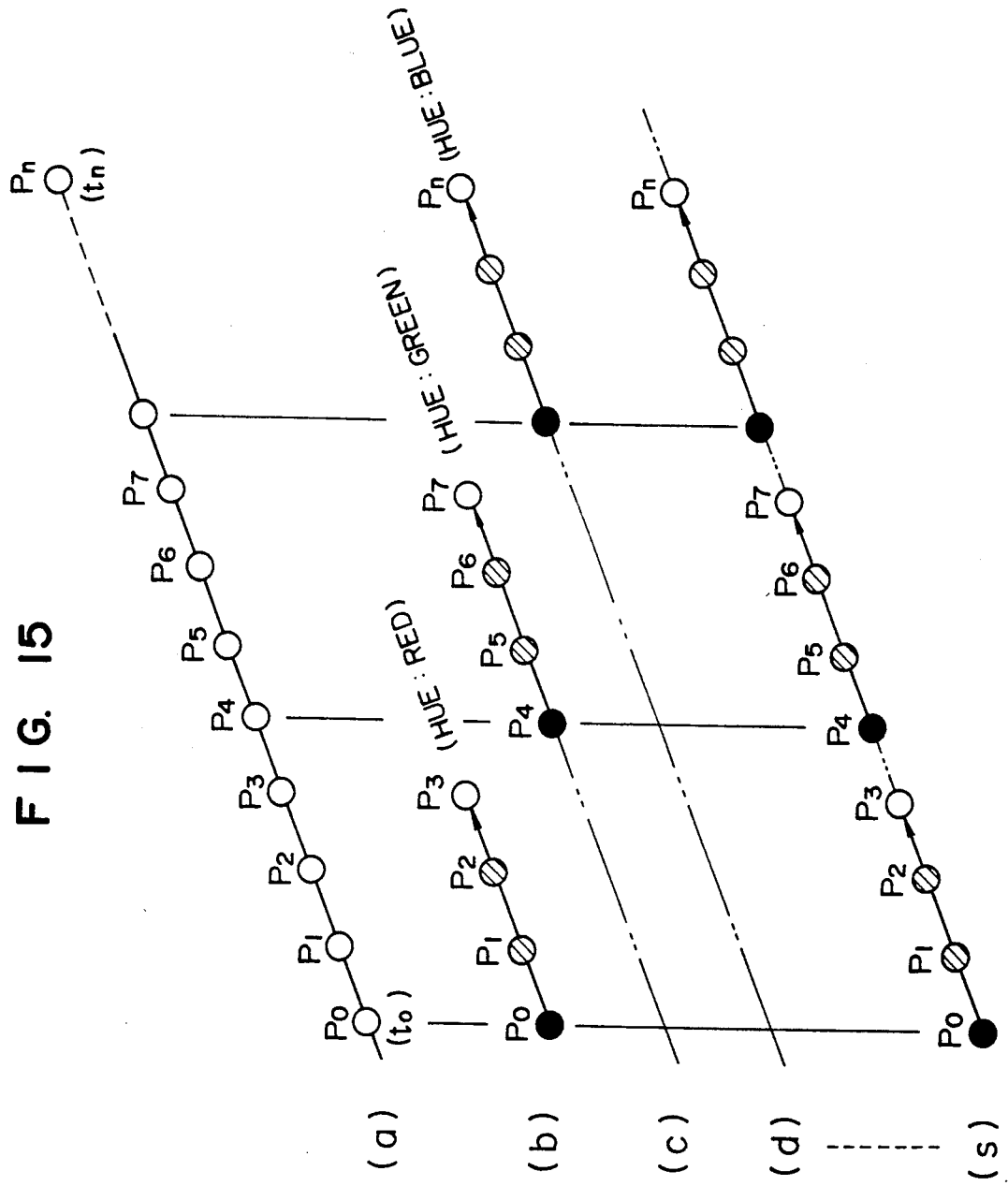
FIG. 15 is a diagram showing a display example of cumulative differential images.

Next, the display mode in the fourth embodiment will be described along with FIG. 15. FIG. 15(a) shows tomographic images $P_0$, $P_1$, $P_2$, . . . , $P_n$ at each time from the time $t_0$ to the time $t_n$, and these tomographic images $P_0$ to $P_n$ are stored in the frame memories $14a$ to $14n$. With respect to tomographic images $P_0$ to $P_n$, differential images are formed for example from $P_0$ and $P_1$, $P_1$ and $P_2$, $P_2$ and $P_3$, . . . , $P_{n-1}$ and $P_n$, respectively, under the command of the controller 17 in a similar manner to that shown (b) to (d) in FIG. 11. Those differential images are stored in the frame memories 9a to 9n.

Next, when differential images are read out from the frame memories 9a to 9n, the controller 11 reads the differential images in the designated number of frames repeatedly by the command of the differential image setting unit 32. Namely, when it is assumed that an operator sets three frames as the differential image addition number of frame setting unit 32, a three frame differential cumulative image composed of $P_0$, $P_1$, $P_2$ and $P_3$ is formed first of all by the cumulative processing circuit 21 as shown in FIG. 15(b), and is outputted to a first storage region of the frame memory 31 after being given a red hue for example by means the color encoder 27. Then, three frames of differential images composed of $P_4$, $P_5$, $P_6$ and $P_7$ are read out of the frame memories 9a to 9n, a differential cumulative image shown in FIG. 15(c) is formed by the cumulative processing circuit 21 and outputted to a second storage region of the frame memory 31 after being given a green hue for example. It is recommended that the hue information given to the second differential cumulative image is made different from the hue of the first differential cumulative image. The reason is to make it easy to discriminate respective vectors when continuous display of vectors is made.

Thereafter, the differential images are read three frames at a time in time series out of the frame memories 9a 9n and cumulated and stored in the frame memory 31 while changing the hue information in a similar manner.

Next, the differential cumulative image is read out of the frame memory 31 and displayed on the image display unit 7 after D/A conversion in such a manner as described hereunder. The display mode will be described in the next place.

In a first display mode, differential cumulative images in respective storage regions of the frame memory 31 are read and displayed as shown in FIG. 15(s). In the image according to such a display method, a plurality of vectors such as shown in FIG. 11(e) are displayed continuously. Further, it becomes easier to discriminate the moving direction and the velocity of the moving tissue by setting the number of added differential images appropriately. In particular, when the present method is applied to the blood stream, a stream of blood corpuscles can be discriminated vector-wise.

In a second display mode, respective differential cumulative images are displayed in a series with images separated by predetermined time. As shown in FIG. 16, first of all, a differential cumulative image composed of $P_0$ to $P_3$ in the first storage region of the frame memory 31 is read and displayed repeatedly for the period of time T at times $t_1^-$ to $t_4^-$ then a differential cumulative image composed of $P_4$ to $P_7$ is read and displayed repeatedly for the period of time T, and the differential cumulative images are displayed in a similar manner thereafter with the lapse of time. According to the second display mode, being different from the above-described first display mode, only the vectors within a certain period of time are displayed for every predetermined period of time. Thus, it is possible to observe only those vectors in all aspects.

Besides, the construction shown in FIG. 14 shows that composite display may be made on the differential cumulative image also with the tomographic image as the background image in the present embodiment.

We claim:

1. An ultrasonic diagnostic apparatus comprising:
   (1) ultrasonic transmitting-receiving means for transmitting and receiving an ultrasonic wave to and from a body to be inspected;
   (2) tomographic scanning means for obtaining tomographic image data of a predetermined portion of said body to be inspected from a reflected echo signal from said ultrasonic transmitting-receiving means in a time series;
   (3) means for generating differential image data of images by performing a differential operation upon said images in said time series which have been obtained by said tomographic scanning means;
   (4) means for providing color codes which designate display colors to said differential image data;
   (5) means for cumulating a plurality of frames of said differential image data; and
   (6) means for displaying said cumulated plurality of frames of said differential image data in colors designated by said color codes.

2. An ultrasonic diagnostic apparatus according to claim 1 further comprising:
   (7) means for detecting biosignals periodically generated form said body to be inspected;
   (8) means for storing data of said biosignals;
   (9) control means for reading and writing data of said biosignals synchronously with said tomographic image data with respect to said storage means;
   (10) means for adding said data to said biosignals to said differential image data; and
   (11) means for reading differential image data corresponding to timing of said biosignals when said timing is designated by an operator on a waveform of said biosignals.

3. An ultrasonic diagnostic apparatus comprising:
   (1) ultrasonic transmitting-receiving means for transmitting and receiving an ultrasonic wave to and from a body to be inspected;
   (2) tomographic scanning means for obtaining tomographic image data of a predetermined portion of said body to be inspected from a reflected echo signal from said ultrasonic transmitting-receiving means in a time series;
   (3) means for generating differential image data of images by performing a differential operation upon said images in said time series which have been obtained by said tomographic scanning means;
   (4) means for weighting at least part of said image data used for generation of differential image data;
   (5) means for cumulating a plurality of frames of said differential image data;
   (6) means for color-encoding said cumulated differential image data; and
   (7) means for displaying said color-encoded cumulative differential image data.

4. An ultrasonic diagnostic apparatus according to claim 3 wherein:
   said weighting means includes means for providing an offset to said differential image data.

5. An ultrasonic diagnostic apparatus according to claim 3, wherein said color-encoding means includes means for color-encoding luminance levels of said cumulated differential images.

6. A method of forming an ultrasonic image comprising the steps of:
   (a) transmitting an ultrasonic wave to a body to be inspected and obtaining tomographic data of a predetermined portion of said body to be inspected in a time series from a received reflected echo signal;

(b) generating differential image data of images by performing a differential operation upon said tomographic image data;

(c) providing color codes for designating display colors to said differential image data;

(d) cumulating a plurality of frames of said differential image data; and (e) displaying said cumulated differential frames in colors designated by said color codes.

7. A method of forming an ultrasonic image according to claim 6 further comprising the steps of:

(f) detecting biosignals periodically generated by said body to be inspected;

(g) storing data of said biosignals;

(h) adding said data of said biosignals to said differential image data; and (i) reading and displaying differential image data corresponding to timing of said biosignals when said timing is designated by an operator on a waveform of said biosignals.

8. A method of forming an ultrasonic image comprising the steps of:

(a) transmitting an ultrasonic wave to a body to be inspected and obtaining tomographic data of a predetermined portion of said body to be inspected in a time series from a received reflected echo signal;

(b) generating differential image data by using parts of said tomographic data with at least one part of said tomographic data being weighted;

(c) weighting said differential image data;

(d) cumulating a plurality of frames of said weighted differential image data;

(e) color-encoding said cumulated differential image data; and (f) displaying said color-encoded cumulated differential image data.

9. A method of forming an ultrasonic image according to claim 8 wherein:

said step of generating differential image data comprises weighting said generated differential image data by providing an offset.

* * * * *